United States Patent [19]

Shilliday

[11] 4,127,940

[45] Dec. 5, 1978

[54] ORTHODONTIST'S INSTRUMENT FOR APPLYING ELASTIC ARCH WIRE-RETAINING RINGS

[76] Inventor: Douglas J. Shilliday, 4848 Slate Run Ct., Columbus, Ohio 43220

[21] Appl. No.: 773,743

[22] Filed: Mar. 2, 1977

[51] Int. Cl.² ............................................. A61C 7/00
[52] U.S. Cl. ........................................................ 32/66
[58] Field of Search ............................................ 32/66

[56] References Cited

U.S. PATENT DOCUMENTS 3,475,818  11/1969  Abrams ................................... 32/66

OTHER PUBLICATIONS

American Journal of Orthodontics, vol. 49, #4, Nov. 1963, p. 32.

Primary Examiner—Robert Peshock
Attorney, Agent, or Firm—William S. Rambo

[57] ABSTRACT

A dentist's instrument or hand tool used to facilitate the application of an elastic arch wire-retaining band or annulus to an arch wire-supporting bracket and which features an elongated handle terminating at one end thereof in an omegoid tip portion arranged to releasably hold the elastic annulus while it is being stretched and applied to the opposite ends of the supporting bracket to retain the arch wire therein.

2 Claims, 12 Drawing Figures

ORTHODONTIST'S INSTRUMENT FOR APPLYING ELASTIC ARCH WIRE-RETAINING RINGS

BACKGROUND OF THE INVENTION

This invention relates generally to dental hand tools or instruments, and more specifically to a dentist's hand tool used to apply an elastic O-ring or annulus in a stretched and tensioned condition to the opposite wings or ends of an arch wire-supporting bracket whereby to hold or retain the arch wire in the bracket.

In the past, the application of conventional, small diameter elastic retaining modules or annuli to the opposite wings of arch wire-supporting brackets has been an extremely tedious job for the orthodontist, and in some cases, a painful experience for the patient. Heretofore, forceps or a hemostat have been employed to grip and apply tension to the elastic annulus as it is being hooked around and stretched between the opposite wings of an arch wire-supporting bracket which is secured to a tooth in the patient's mouth. Oftentimes, the forceps or hemostat will accidentally slip and release or break the tensioned annulus and knock the bracket loose from the tooth or rebound against the patient's mouth with harmful and painful results.

SUMMARY AND OBJECTS OF THE INVENTION

This invention provides an improved hand tool or instrument for applying elastic annuli to arch wire-supporting brackets within the mouth. The present instrument consists of a unitary handpiece which includes an elongated handle portion having at one end thereof an omegoid tip portion on which an elastic annulus may be placed and carried to the arch wire-supporting bracket within the patient's mouth. The omegoid tip enables the orthodontist to hook one side of the annulus around the retaining wings on one side of the bracket while the annulus is still on the tip of the tool, and then, by a simple rotary motion of the fingers, to release and engage the other side of the annulus with the retaining wings formed on the opposite side of the bracket.

The primary object of this invention is to provide a hand tool or instrument which facilitates the application of conventional elastic retaining rings to arch wire-supporting brackets within a patient's mouth.

Another object is to provide an orthodontist's hand tool of the aforementioned character which is both structurally simple and easily operated.

Additional objects and advantages of the invention will become more apparent by reference to the following description and the accompanying drawings.

DESCRIPTION OF PREFERRED EMBODIMENT OF THE INVENTION

Figure 1:
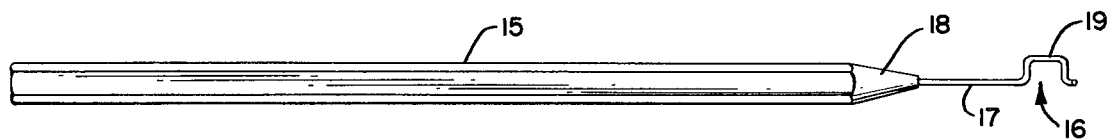
FIG. 1 is a side elevational view of an orthodontist's hand tool according to this invention.
Figure 2:
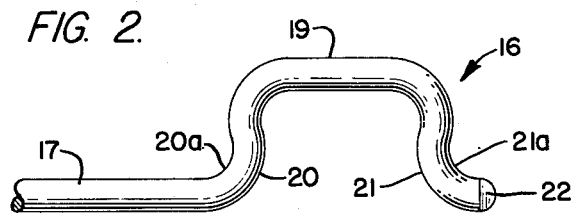
FIG. 2 is an enlarged, fragmentary side elevational view of the operative tip portion of the tool.
Figure 3:
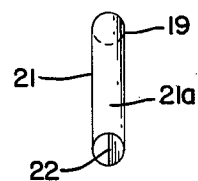
FIG. 3 is an end elevational view of the tip portion.

Referring to FIG. 1, it will be seen that the present orthodontist's hand tool or instrument comprises a unitary body or structure which includes an elongated, substantially straight, rigid handle section 15 and an operative tip section 16. The handle section preferably has an octagonal or other multi-angular outer surface and is similar in size and configuration to the handle of the usual dentist's pick or point. However, the tip section 16 of the present tool is quite different as will be hereinafter explained. The tip section 16 is preferably formed from stainless steel or other noncorrosive metallic alloy wire of a gauge or diameter sufficient to make it substantially inflexible. The tip section 16 includes an intermediate, straight shank portion 17 which is welded, screw-threaded into, or otherwise rigidly and permanently connected with the tapered end portion 18 of the handle section.

The tip section 16 is formed at the outer end of its shank portion 17 with a transverse or laterally offset bight 19 which includes a pair of opposed, relatively spaced apart side legs 20 and 21. The side legs 20 and 21 are curved slightly inwardly toward one another, so as to form undercut or concave recesses 20a and 21a on the outer surface of each side leg. The outermost side leg 21 terminates in a relatively short, beveled point 22 disposed in axial alignment with the straight shank portion 17. Viewed in side elevation, the tip section 16 has an omegoid shape, i.e. it resembles the Greek capital letter, omega-($\Omega$).

Operation

As previously indicated, the present orthodontist's hand tool or instrument is used to apply conventional elastic archwire-retaining bands or annuli 25 to conventional, metallic supporting brackets 26 which are adhesively secured to the outer or labial surfaces 27 of the teeth 28 within a human mouth. A conventional metal arch wire or band 29 is held in predetermined, corrective relation to the teeth by the brackets 26 and the elastic annuli function to retain the archwire 29 in the brackets 26. As shown more particularly in FIGS. 6, 8, 10 and 12, each of the brackets 26 is formed to include a substantially flat, rectangular base portion 30 which is cemented or adhesively secured to the labial surface 27 of the tooth 28. The bracket is also formed with a pair of relatively spaced apart, forwardly projecting cleats 31 which terminate in opposite hook-shaped ends or wings 32 disposed in outwardly spaced relation to the base portion 30. Each of the cleats 31 is formed with a centrally located, outwardly opening notch or recess 33 to receive the arch wire 29 and to permit it to pass laterally outwardly to either side of the bracket.

Figure 4:
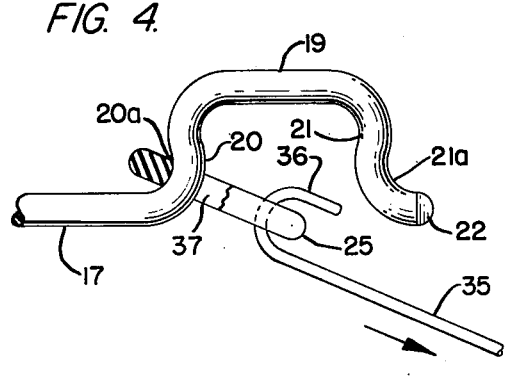
FIGS. 4 and 5 are side elevational views similar to FIG. 2, but showing, sequentially, the preferred method of placing an elastic annulus on the tip portion of the hand tool.

Each of the elastic bands or annuli 25 consists of a small (approx. 3mm. outer diameter) O-ring of rubber or elastomeric synthetic resin material. The annuli 25 are usually packaged and supplied in stacks of fifty or more carried on an elongated rigid wire carrier 35 having a hook-shaped outer end 36. FIG. 4 shows one of the elastic bands 25 in process of being transferred from the carrier 35 to the tip 16 of the present hand tool preparatory to applying the band to a selected arch-wire-supporting bracket 26. The outermost band 25 of the stack of bands is moved onto the hooked end 36 of the carrier 35. Then, starting with the beveled end 22, the bight portion 19 of the hand tool is passed through the eye or central opening in the band 25 until one side of the band comes to rest in the recess 20a of the side leg 20 of the tip. While the opposite side of the band 25 is still engaged with the hooked end 36 of the carrier 35, the carrier is moved relatively outwardly in the direction of the arrow shown in FIG. 4 to stretch and elongate the band 25 to a length where hook-engaged end of the band may be stretched over the beveled end 22 of the tool tip. At this point, the carrier 35 is rotated counterclockwise to the position shown in FIG. 5 to permit the opposite end of the band to snap free of the hooked end 36 of the carrier and into the recess 21a of the leg 21 of the tip. Thus, through a simple combined manipulation of the carrier 35 and the hand tool, an annulus 25 may be easily transferred from the supply carrier 35 and deposited in tensioned condition over the bight 19 of the hand tool without actually grasping the small band 25 between the fingers of the hand.

Figure 5:
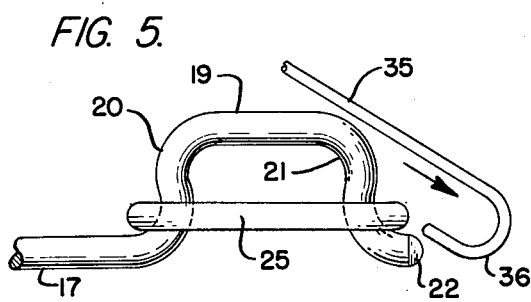
Figure 6:
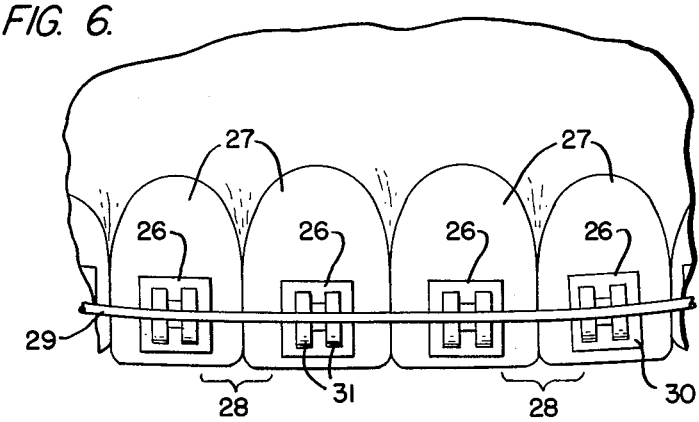
FIG. 6 is a fragmentary elevational view of a group of teeth having support brackets secured thereto with an arch wire spanning the teeth and brackets prior to the application of elastic retaining bands or annuli to the brackets.
Figure 7:
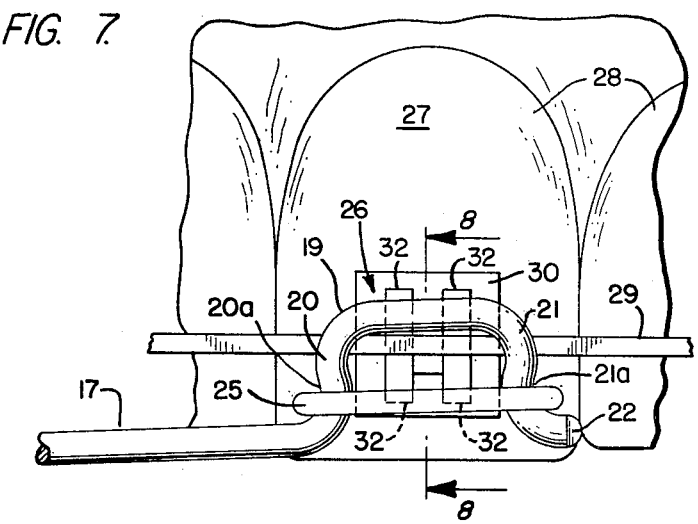
FIGS. 7, 9 and 11 are similar side elevational views illustrating sequentially the way in which the tool is manipulated to apply an elastic annulus to an arch wire-supporting bracket.
Figure 8:
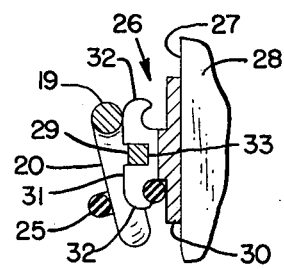
FIGS. 8, 10 and 12 are similar, transverse vertical sectional views taken along the lines 8—8, 10—10 and 12—12 of FIGS. 7, 9 and 11, respectively.
Figure 9:
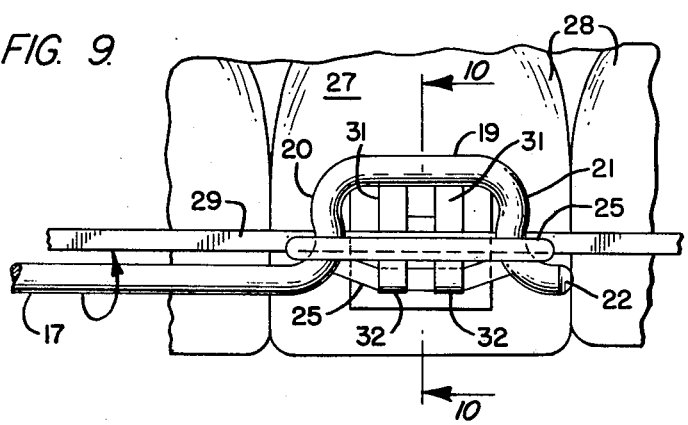
Figure 10:
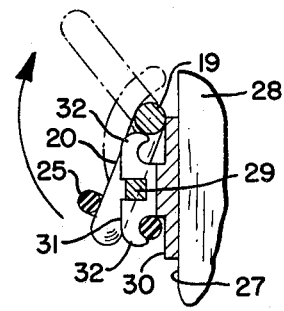
Figure 11:
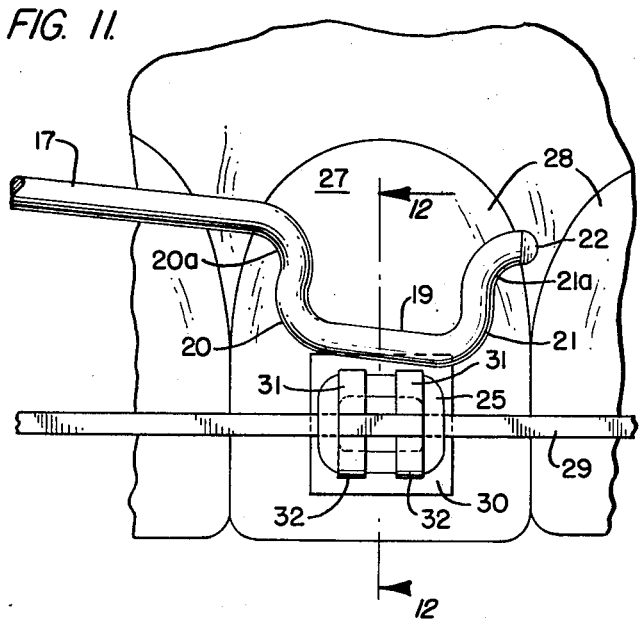
Figure 12:
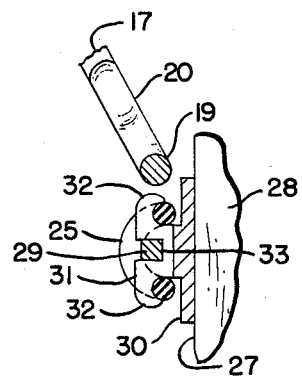

With the tensioned band 25 positioned on the tip of the tool, as shown in FIG. 5, the band is in readiness for application to a selected bracket 26. FIGS. 7 through 12 illustrate the sequence of manipulative steps for transferring the tensioned band from the present tool and applying it in desired position to the wings 32 of a selected bracket. FIGS. 7 and 8 show the tip 16 of the tool in position to place one side of the band or annulus 25 behind the lower set of hook-shaped wings 32 of the bracket 26. FIGS. 9 and 10 show the bight 19 of the tool being moved upwardly to a position where it will rest and pivot on the upper set of wings 32, with one side of the elastic band 25 still engaged with the lower set of wings. Now, as the tip 16 of the tool is rotated clockwise from the position shown in FIGS. 9 and 10 to the position shown in FIGS. 11 and 12, the band 25 will be stretched around the arch wire 29 and the tension in the stretched band 25 will cause it to slide off and snap free of the bight 19 of the tip 16 and snap into position behind the upper set of wings 32 as the tip reaches an inverted position. In this regard, it will be understood that FIGS. 11 and 12 illustrate the final applied position of the elastic band 25 on the bracket 26. The present tool may then be used in the same manner to apply additional elastic bands 25 to the remaining brackets 26 to thus retain the arch wire 29 in desired spanning relation to the teeth 28.

In view of the foregoing, it will be seen that the present invention provides a mechanically simple, yet highly efficient hand tool or instrument to assist the orthodontist in the application of elastic archwire-retaining rings or annuli to the archwire-support brackets of an orthodontic archwire assembly.

While a single preferred embodiment of the invention and its mode of operation have been illustrated and described in detail, it will be understood that various modifications in design and details of construction may be resorted to without departing from the spirit of the invention or the scope of the following claims.

I claim:

1. An orthodontist's instrument for applying an elastic retaining band comprising a relatively elongated handle and a wire-like operative tip rigidly connected with and projecting outwardly from an end of said handle; said tip consisting of a single, substantially rigid wire formed with a generally U-shaped, laterally projecting bight portion having opposed, relatively spaced apart side legs curved slightly inwardly toward one another and defining on the bight portion of said tip a relatively shallow undercut region for the readily releaseable support of an encircling, tensioned, elastic band.

2. An orthodontist's instrument according to claim 1, wherein the bight portion of said tip is formed in the shape of the Greek capital letter, omega.

* * * * *